US 9,257,264 B2

(12) United States Patent
Hummel et al.

(10) Patent No.: US 9,257,264 B2
(45) Date of Patent: Feb. 9, 2016

(54) HARMONIC COLD PLASMA DEVICES AND ASSOCIATED METHODS

(75) Inventors: Robert M. Hummel, Cave Creek, AZ (US); Gregory A. Watson, Lake Mary, FL (US); Marc C. Jacofsky, Phoenix, AZ (US); David J. Jacofsky, Peoria, AZ (US)

(73) Assignee: Plasmology4, Inc., Scottsdale, AZ (US)

( * ) Notice: Subject to any disclaimer, the term of this patent is extended or adjusted under 35 U.S.C. 154(b) by 520 days.

(21) Appl. No.: 13/620,132

(22) Filed: Sep. 14, 2012

(65) Prior Publication Data

US 2013/0069530 A1 Mar. 21, 2013

Related U.S. Application Data

(60) Provisional application No. 61/535,250, filed on Sep. 15, 2011.

(51) Int. Cl.
*H01J 7/24* (2006.01)
*H01J 37/32* (2006.01)
(Continued)

(52) U.S. Cl.
CPC ............ *H01J 37/321* (2013.01); *A61L 2/00* (2013.01); *A61L 2/0094* (2013.01); *A61L 2/14* (2013.01); *A61M 15/02* (2013.01); *A61M 16/06* (2013.01); *A61M 16/12* (2013.01); *A61N 1/40* (2013.01); *A61N 1/44* (2013.01); *H01J 37/3244* (2013.01); *H01J 37/3266* (2013.01); *H01J 37/32348* (2013.01); *H05H 1/2406* (2013.01); *H05H 1/46* (2013.01); *A61M 2202/025* (2013.01); *A61M 2202/0208* (2013.01); *H05H 2001/2412* (2013.01); *H05H 2001/466* (2013.01); *H05H 2001/4682* (2013.01); *H05H 2240/20* (2013.01);
(Continued)

(58) Field of Classification Search
CPC .......................... H03H 1/46; H01J 37/32082
See application file for complete search history.

(56) References Cited

U.S. PATENT DOCUMENTS 2,927,322 A   3/1960 Simon et al.
3,432,722 A   3/1969 Naydan et al.
(Continued)

FOREIGN PATENT DOCUMENTS

EP   0 508 482 A2   10/1992
EP   1 117 279 A1    7/2001
(Continued)

OTHER PUBLICATIONS

International Search Report mailed Mar. 29, 2013 for Appl. No. PCT/US2012/55571, 3 pages.
(Continued)

*Primary Examiner* — Ryan Jager
(74) *Attorney, Agent, or Firm* — Sterne, Kessler, Goldstein & Fox P.L.L.C.

(57) ABSTRACT

A gas cartridge is described that is configured to provide sufficient gas to support cold plasma generation for a specific medical process. The gas cartridge has a seal that is pierced upon connection of the gas cartridge to the cold plasma delivery system. Different embodiments are described that use different connection locations between the gas cartridge and the cold plasma delivery system. A shroud is also described that shields the user if the cold plasma delivery system is dropped and the gas cartridge ruptures. Use of an ID system assists in ensuring that the correct gas mixture, correct gas cartridge and correct power supply settings are used for the particular medical treatment process.

23 Claims, 11 Drawing Sheets

(51) Int. Cl.

| | | |
|---|---|---|
| A61M 16/06 | (2006.01) | |
| A61M 16/12 | (2006.01) | |
| A61M 15/02 | (2006.01) | |
| A61N 1/44 | (2006.01) | |
| H05H 1/24 | (2006.01) | |
| A61N 1/40 | (2006.01) | |
| A61L 2/00 | (2006.01) | |
| H05H 1/46 | (2006.01) | |
| A61L 2/14 | (2006.01) | |

(52) U.S. Cl.
CPC .... *H05H 2245/1225* (2013.01); *H05H 2277/10* (2013.01)

(56) References Cited

U.S. PATENT DOCUMENTS

| | | |
|---|---|---|
| 3,487,414 A | 12/1969 | Booker |
| 3,735,591 A | 5/1973 | Burkhart |
| 4,088,926 A | 5/1978 | Fletcher et al. |
| 4,365,622 A | 12/1982 | Harrison |
| 4,380,320 A | 4/1983 | Hollstein et al. |
| 4,422,013 A | 12/1983 | Turchi et al. |
| 5,079,482 A | 1/1992 | Villecco et al. |
| 5,216,330 A | 6/1993 | Ahonen |
| 5,225,740 A | 7/1993 | Ohkawa |
| 5,304,888 A | 4/1994 | Gesley et al. |
| 5,669,904 A | 9/1997 | Platt, Jr. et al. |
| 5,698,164 A | 12/1997 | Kishioka et al. |
| 5,876,663 A | 3/1999 | Laroussi |
| 5,883,470 A | 3/1999 | Hatakeyama et al. |
| 5,909,086 A | 6/1999 | Kim et al. |
| 5,961,772 A | 10/1999 | Selwyn |
| 5,977,715 A | 11/1999 | Li et al. |
| 6,096,564 A | 8/2000 | Denes et al. |
| 6,113,851 A | 9/2000 | Soloshenko et al. |
| 6,204,605 B1 | 3/2001 | Laroussi et al. |
| 6,225,593 B1 | 5/2001 | Howieson et al. |
| 6,228,330 B1 | 5/2001 | Herrmann et al. |
| 6,262,523 B1 | 7/2001 | Selwyn et al. |
| 6,441,554 B1 | 8/2002 | Nam et al. |
| 6,455,014 B1 | 9/2002 | Hammerstrom et al. |
| 6,611,106 B2 | 8/2003 | Monkhorst et al. |
| 6,667,007 B1 | 12/2003 | Schmidt |
| 6,956,329 B2 | 10/2005 | Brooks et al. |
| 6,958,063 B1 | 10/2005 | Soll et al. |
| 7,006,874 B2 | 2/2006 | Knowlton et al. |
| 7,011,790 B2 | 3/2006 | Ruan et al. |
| 7,037,468 B2 | 5/2006 | Hammerstrom et al. |
| 7,081,711 B2 | 7/2006 | Glidden et al. |
| 7,094,314 B2 | 8/2006 | Kurunczi |
| 7,192,553 B2 | 3/2007 | Crowe et al. |
| 7,215,697 B2 | 5/2007 | Hill |
| 7,271,363 B2 | 9/2007 | Lee et al. |
| 7,300,436 B2 | 11/2007 | Penny et al. |
| 7,608,839 B2 | 10/2009 | Coulombe et al. |
| 7,633,231 B2* | 12/2009 | Watson .................. 315/111.51 |
| 7,681,572 B2* | 3/2010 | Fishman .................. 128/203.12 |
| 7,683,342 B2 | 3/2010 | Morfill et al. |
| 7,691,101 B2 | 4/2010 | Davison et al. |
| 7,719,200 B2 | 5/2010 | Laroussi |
| 7,777,151 B2 | 8/2010 | Kuo |
| 7,785,322 B2 | 8/2010 | Penny et al. |
| 7,799,290 B2 | 9/2010 | Hammerstrom et al. |
| 8,267,884 B1 | 9/2012 | Hicks |
| 8,294,369 B1 | 10/2012 | Laroussi |
| 8,460,283 B1 | 6/2013 | Laroussi et al. |
| 2002/0129902 A1 | 9/2002 | Babayan et al. |
| 2003/0222586 A1 | 12/2003 | Brooks et al. |
| 2005/0088101 A1 | 4/2005 | Glidden et al. |
| 2005/0179395 A1 | 8/2005 | Pai |
| 2006/0189976 A1 | 8/2006 | Karni et al. |
| 2007/0062510 A1* | 3/2007 | Broersma ....................... 124/74 |
| 2007/0065706 A1 | 3/2007 | Adams et al. |
| 2008/0159925 A1 | 7/2008 | Shimizu et al. |
| 2009/0012589 A1* | 1/2009 | Watson ........................... 607/99 |
| 2009/0188626 A1 | 7/2009 | Lu et al. |
| 2010/0133979 A1 | 6/2010 | Lu |
| 2010/0275950 A1 | 11/2010 | Mack et al. |
| 2011/0022043 A1 | 1/2011 | Wandke et al. |
| 2011/0054454 A1* | 3/2011 | Rooks et al. ..................... 606/27 |
| 2011/0105952 A1 | 5/2011 | Bernstein et al. |
| 2012/0100524 A1 | 4/2012 | Fridman et al. |
| 2012/0187841 A1 | 7/2012 | Kindel et al. |
| 2012/0259270 A1 | 10/2012 | Wandke et al. |
| 2012/0276499 A1* | 11/2012 | Devery et al. ................... 433/32 |
| 2013/0022514 A1 | 1/2013 | Morfill et al. |
| 2013/0053762 A1 | 2/2013 | Rontal et al. |
| 2013/0072860 A1* | 3/2013 | Watson et al. .................. 604/23 |
| 2013/0134878 A1 | 5/2013 | Selwyn |
| 2013/0199540 A1 | 8/2013 | Buske |
| 2014/0000810 A1 | 1/2014 | Franklin et al. |
| 2014/0044805 A1* | 2/2014 | Kiss ............................ 424/700 |

FOREIGN PATENT DOCUMENTS

| | | |
|---|---|---|
| WO | WO 2004102065 A2 * | 11/2004 |
| WO | WO 2005/084569 A1 | 9/2005 |
| WO | WO 2006/116252 | 11/2006 |
| WO | WO 2007/124910 A2 | 11/2007 |
| WO | WO 2010.107722 A1 | 9/2010 |
| WO | WO 2011/055368 A2 | 5/2011 |
| WO | WO 2011/055369 A2 | 5/2011 |
| WO | WO 2011/076193 A1 | 6/2011 |
| WO | WO 2012/106735 A2 | 8/2012 |
| WO | WO 2012/153332 A2 | 11/2012 |
| WO | WO 2013/101673 A1 | 7/2013 |

OTHER PUBLICATIONS

Written Opinion of International Searching Authority mailed Mar. 29, 2013 for Appl. No. PCT/US2012/55571, 5 pages.

Fridman et al., "Comparison of Direct and Indirect Effects of Non-Thermal Atmospheric-Pressure Plasma on Bacteria," *Plasma Processl Polym.*, 4, 370-375, 6 pages, Wiley-VCH Verlag GmbH & Co. KGaA, Weinheim (2007).

Alexander Fridman, "Plasma Chemistry," pp. 263-271, Cambridge University Press, 2008, 9 pages.

O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).

Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).

Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).

Walsh et al., "Three distinct modes in a cold atmospheric pressure plasma jet," *J. Phys. D.: Appl. Phys.* 43 075201, 14 pages, IOP Publishing Ltd (Feb. 3, 2010).

Ricci et al., "The effect of stochastic electrical noise on hard-to-heal wounds," *Journal of Wound Care*, 8 pages, 19:3 Mark Allen Publishing Ltd ( Mar. 2010).

U.S. Appl. No. 61/485,747, filed May 13, 2011, inventor Thomas J. Sheperak, 14 pages.

Liu et al., "Sub-60° C. atmospheric helium-water plasma jets: modes, electron heating and downstream reaction chemistry," *J. Phys. D: Appl. Phys.* 44 345203, 13 pages, IOP Publishing Ltd. (Aug. 11, 2011).

Pei et al., "Inactivation of a 25.5 μm Enterococcus faecalis biofilm by a room-temperature, battery-operated, handheld air plasma jet," *J. Phys. D. Appl. Phys.*, 45 165205, 5 pages, IOP Publishing Ltd (Apr. 4, 2012).

Walsh et al., "Chaos in atmospheric-pressure plasma jets," *Plasma Sources Sci. Technol.*, 21 034008, 8 pages, IOP Publishing Ltd (May 2, 2012).

(56) References Cited

OTHER PUBLICATIONS

Banu, et al., "Cold Plasma as a Novel Food Processing Technology," *International Journal of Emerging trends in Engineering and Development*, Issue 2, vol. 4, ISSN 2249-6149, pp. 803-818, 16 pages (May 2012).
Dobrynin, et al., "Live Pig Skin Tissue and Wound Toxicity of Cold Plasma Treatment," *Plasma Medicine*, 1(1):93-108, 16 pages, Begell House, Inc. (2011).
Fernández, et al., "The inactivation of *Salmonella* by cold atmosphere plasma treatment," *Food Research International*, 45:2, 678-684, 7 pages, Elsevier Ltd. (Mar. 2012).
Tien, et al., "The Bilayer Lipid Membrane (BLM) Under Electrical Fields," *IEEE Transactions on Dielectrics and Electrical Institute*, 10:5, 717-727, 11 pages (Oct. 2003).
Jayaram, et al.., "Optimization of Electroporation Waveforms for Cell Sterilization," *IEEE Transactions on Industry Applications*, 40:6, 1489-1497, 9 pages (2004).
Fridman, et al., "Use of Non-Thermal Atmospheric Pressure Plasma Discharge for Coagulation and Sterilization of Surface Wounds," *IEEE International Conference on Plasma Science*, Abstract, p. 257, 1 page (Jun. 2005).
Fridman, et al., "Use of Non-Thermal Atmospheric Pressure Plasma Discharge for Coagulation and Sterilization of Surface Wounds," 6 pages (Jun. 2005).
Fridman, et al., "Blood Coagulation and Living Tissue Sterilization by Floating-Electrode Dielectric Barrier Discharge in Air," *Plasma Chem Plasma Process*, 26: 425-442, 18 pages, Springer Science Business Media, Inc. (2006).
Gurol, et al., "Low Temperature Plasma for decontamination of *E. coli* in milk," *International Journal of Food Microbiology*, 157: 1-5, 5 pages, Elsevier B.V. (Jun. 2012).
Lado, et al., "Alternative food-preservation technologies: efficacy and mechanisms," *Microbes and Infection*, 4: 433-440 8 pages, Elsevier SAS (2002).
Leduc, et al., "Cell permeabilization using a non-thermal plasma," *New Journal of Physics*, 11: 115021, 12 pages, IOP Publishing Ltd and Deutsche Physikalische Gesellschaft (2009).
Machado, et al., "Moderate electric fields can inactivate *Escherichia coli* at room temperature," *Journal of Food Engineering*, 96: 520-527, 8 pages, Elsevier Ltd. (2009).
Li, et al., "Optimizing the distance for bacterial treatment using surface micro-discharge plasma," *New Journal of Physics*, 14: 023058, 11 pages, IOP Publishing Ltd and Deutsche Physikalische Gesellschaft (Feb. 2012).
Morfill, et al., "Nosocomial infections—a new approach towards preventive medicine using plasmas," *New Journal of Physics*, 11: 115019, 10 pages, IOP Publishing Ltd and Deutsche Physikalische Gesellschaft (2009).
Nian, et al., "Decontamination of *Salmonella* on Sliced Fruits and Vegetables Surfaces using a Direct-Current, Atmospheric-Pressure Cold Plasma," *IEEE International Conference on Plasma Science*, p. 1, 1 page (Jun. 2011).
Toepfl, et al., "High intensity pulsed electric fields applied for food preservation," *Chemical Engineering and Processing*, 46: 537-546, 10 pages, Elsevier B.V. (2007).
Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.
Gould, Phillip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.
Schultz, James, "Cold Plasma Ignites Hot Applications," article, [online], [retrieved on Jan. 5, 2007], Retrieved from the Old Dominion University website using Internet <URL:http://www.odu.edu/ao/instadv/quest/coldplasma.html>.
Lamba, Bikram, "Advent of Cold Plasma," article, [online], [retrieved on Jan. 5, 2007], Retrieved from the PhysOrg.com website using Internet <URL:http/www.physorg.com/printnews.php?newsid=6688>.
Book of Abstracts, 3rd International Conference on Plasma Medicine (ICPM-3), Sep. 19-24, 2010, International Society for Plasma Medicine.
International Search Report issued Aug. 6, 2008 for Appl. No. PCT/US2008/061240, 1 page.
Written Opinion of International Searching Authority issued Aug. 6, 2008 for Appl. No. PCT/US2008/061240, 6 pages.
Extended European Search Report issued Feb. 8, 2012 for European Patent Appl. No. EP08746627.2, 7 pages.
Pointu et al., "Nitrogen Atmospheric Pressure Post Discharges for Surface Biological Decontamination inside Small Diameter Tubes," *Plasma Process. Polym*. 5:559-568, Wiley-VCH Verlag GmbH & Co. KGaA, Weinheim (2008).
Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).
The Supplementary European Search Report mailed Jan. 13, 2015 for Appl. No. PCT/US2012/055571, 10 pages.
English-language abstract for: F. Remy, EP 1 117 279 A1 (listed on accompanying PTO/SB/08a as document FP12).

\* cited by examiner

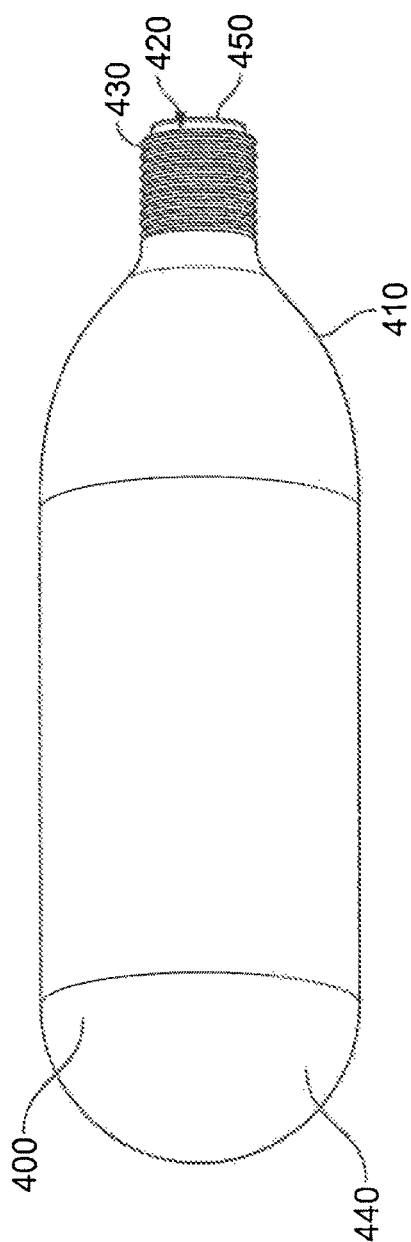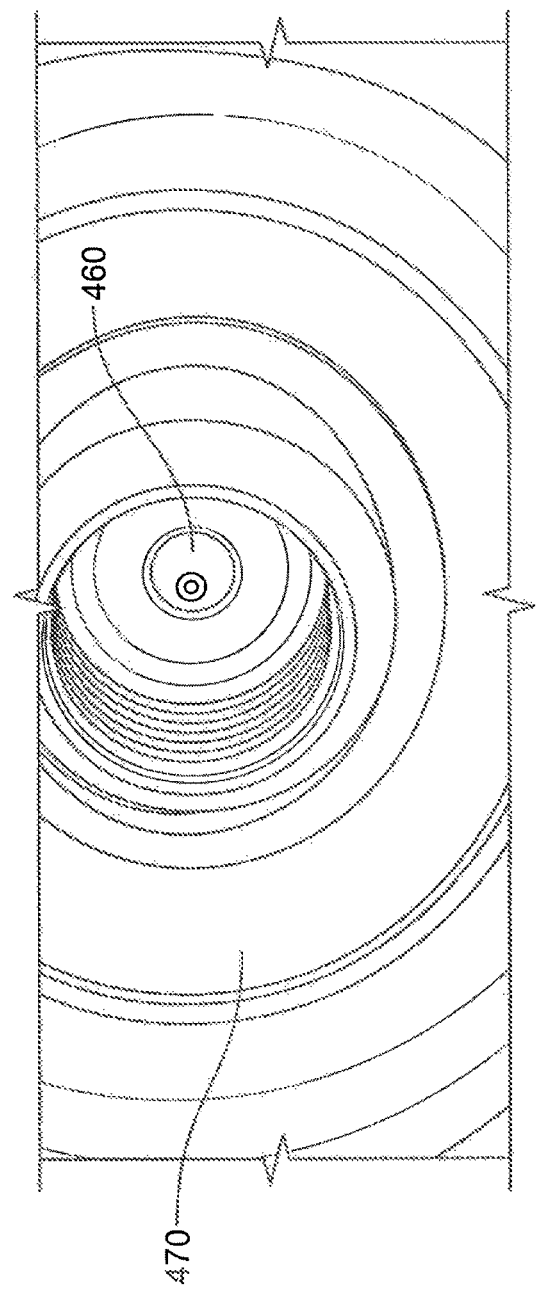
FIG. 4A
FIG. 4B

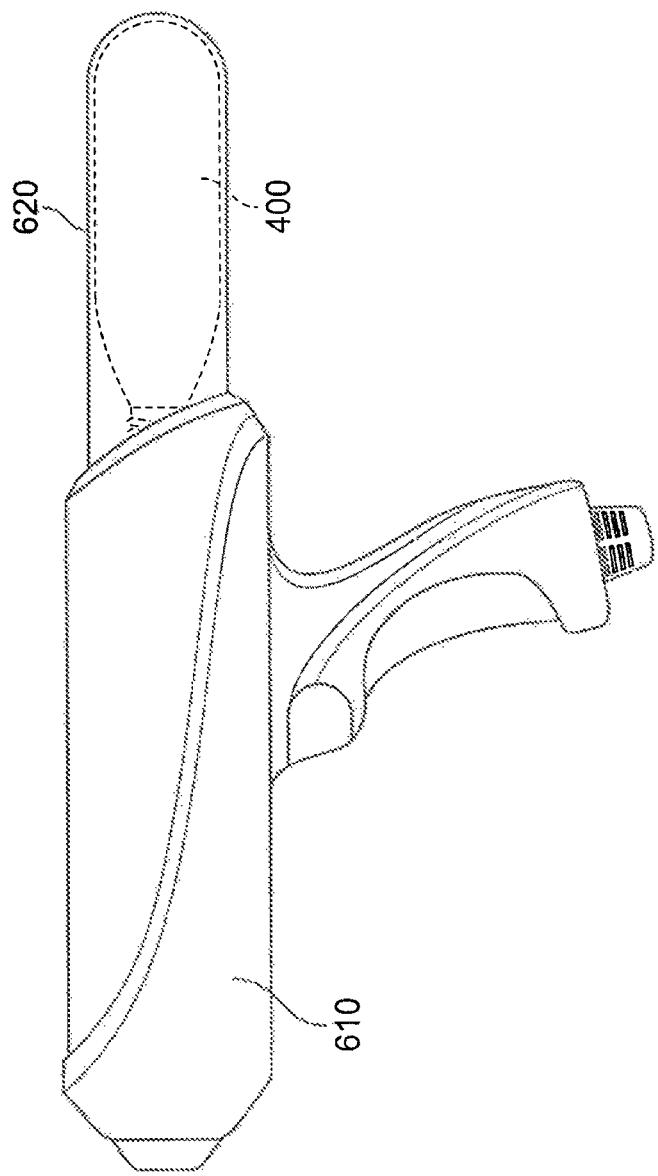

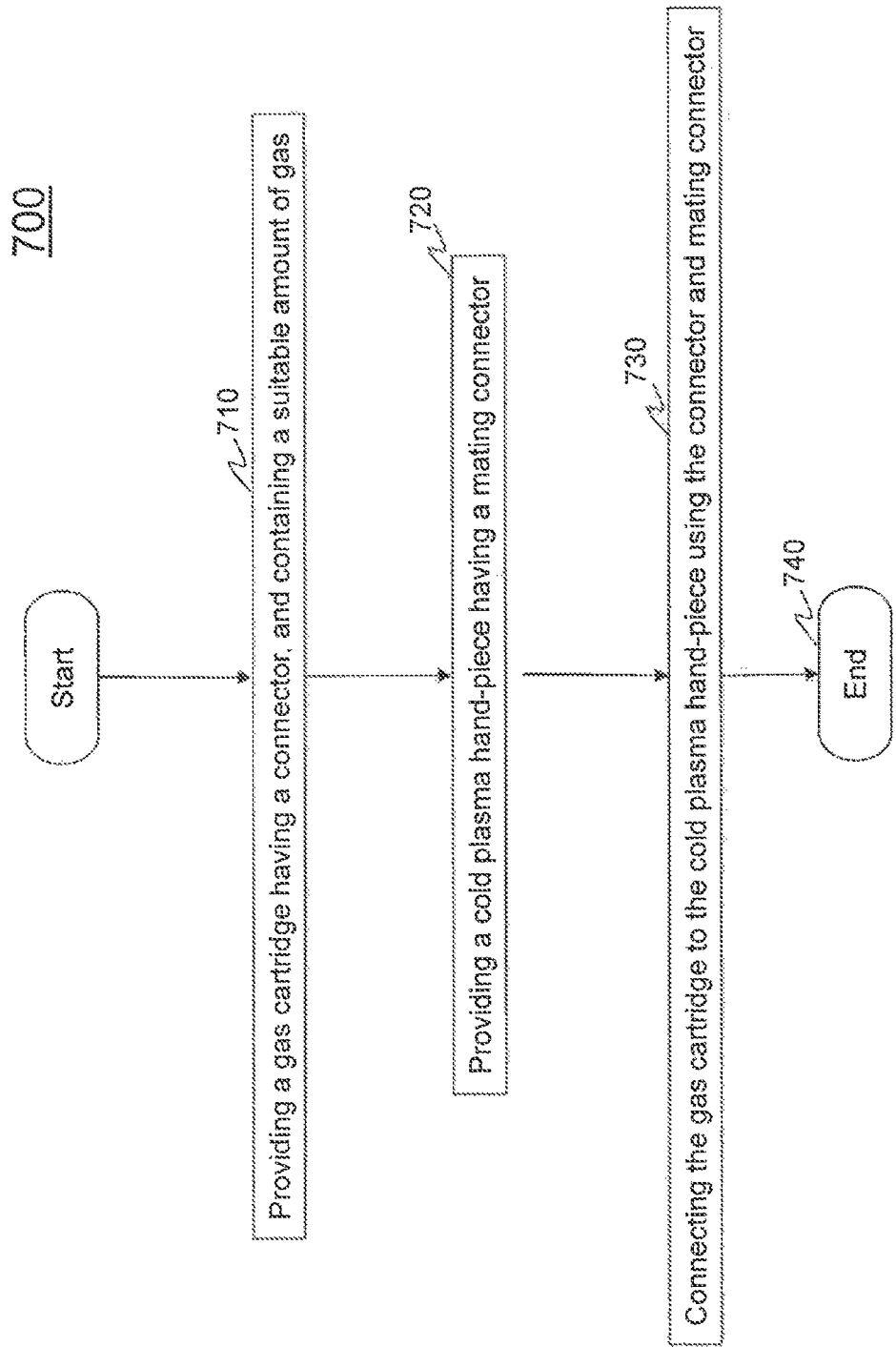

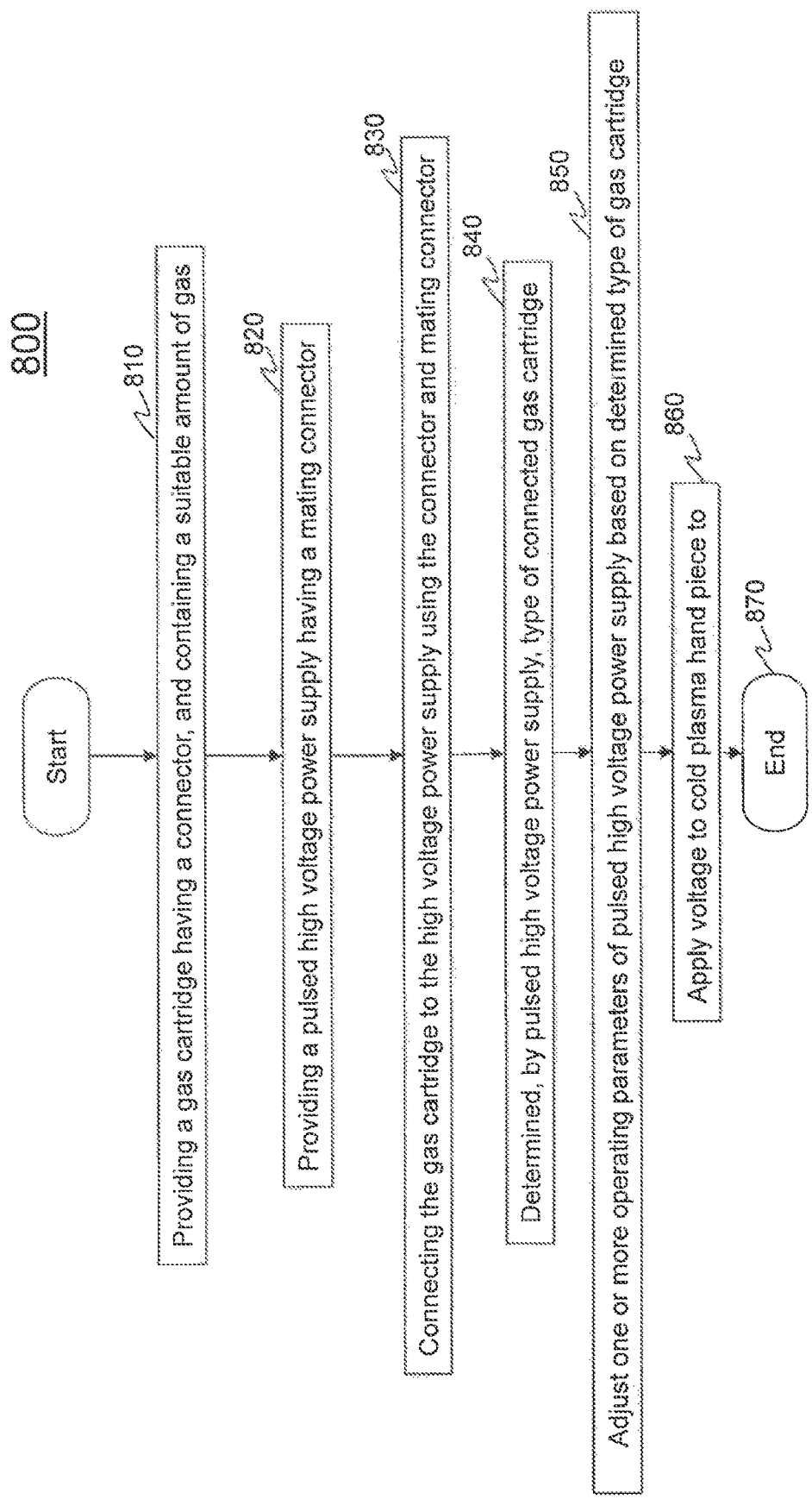

HARMONIC COLD PLASMA DEVICES AND ASSOCIATED METHODS

CROSS REFERENCE TO RELATED APPLICATIONS

The present application claims the benefit under 35 U.S.C. §119(e) of U.S. Provisional Patent Application No. 61/535,250, entitled "Harmonic Cold Plasma Devices and Associated Methods", filed on Sep. 15, 2011, which is hereby expressly incorporated by reference in its entirety.

This application is related to U.S. patent application Ser. No. 13/149,744, filed May 31, 2011, U.S. patent application Ser. No. 12/638,161, filed Dec. 15, 2009, U.S. patent application Ser. No. 12/038,159, filed Feb. 27, 2008, and U.S. Provisional Application No. 60/913,369, filed Apr. 23, 2007, each of which are herein incorporated by reference in their entireties.

BACKGROUND

1. Field of the Art

The present invention relates to devices and methods for creating cold plasmas, and, more particularly, to such devices that are hand-held and methods for using same.

2. Background Art

Atmospheric pressure hot plasmas are known to exist in nature. For example, lightning is an example of a DC arc (hot) plasma. Many DC arc plasma applications have been achieved in various manufacturing processes, for example, for use in forming surface coatings. Atmospheric pressure cold plasma processes are also known in the art. Most of the at or near atmospheric pressure cold plasma processes are known to utilize positive to negative electrodes in different configurations, which release free electrons in a noble gas medium.

Devices that use a positive to negative electrode configuration to form a cold plasma from noble gases (helium, argon, etc.) have frequently exhibited electrode degradation and overheating difficulties through continuous device operation. The process conditions for enabling a dense cold plasma electron population without electrode degradation and/or overheating are difficult to achieve.

Cold plasma devices can be used in a number of different medical treatments relevant to a number of different applications. It is desirable to ensure safe operation and effectiveness of treatment, as well as the purity and sterility of the feed gas.

Therefore, it would be beneficial to provide a device for producing a cold plasma that overcomes the difficulties inherent in prior known devices.

BRIEF SUMMARY OF THE INVENTION

In an embodiment of the present invention, a gas cartridge is described that has a storage compartment for use with a cold plasma device, where the storage compartment is configured to store a quantity of gas suitable for use in a cold plasma hand-piece. The gas cartridge includes a connector having a seal across the outlet, such that the seal is configured to be broken upon connection of the gas cartridge with the cold plasma hand-piece or the associated power supply.

In an embodiment of the present invention, a cold plasma delivery system is described that includes a gas cartridge and a cold plasma hand piece. The gas cartridge has a storage compartment for use with a cold plasma device, where the storage compartment is configured to store a quantity of gas suitable for use in a cold plasma device. The gas cartridge includes a connector having a seal across the outlet, such that the seal is configured to be broken upon connection of the gas cartridge with the cold plasma device or the associated power supply.

In embodiments of the present invention, a cold plasma delivery system is described that includes a gas cartridge and a cold plasma hand piece. Various embodiments include connections of the gas cartridge at the hand-grip and at the rearward end of the cold plasma hand piece.

BRIEF DESCRIPTION OF THE DRAWINGS/FIGURES

FIGS. 4A and 4B illustrate a gas cartridge for use with a cold plasma device, in accordance with embodiments of the present invention.

FIG. 6 illustrates a safety shroud that encloses an attached gas cartridge within a cold plasma delivery system, in accordance with an embodiment of the present invention.

FIG. 7 illustrates a method of use of a gas cartridge within a cold plasma hand-piece, in accordance with an embodiment of the present invention.

FIG. 8 illustrates a method of use of a gas cartridge that connects to the high voltage power supply, in accordance with an embodiment of the present invention.

DETAILED DESCRIPTION OF THE INVENTION

Cold temperature atmospheric pressure plasmas have attracted a great deal of enthusiasm and interest by virtue of their provision of plasmas at relatively low gas temperatures. The provision of a plasma at such a temperature is of interest to a variety of applications, including wound healing, antibacterial processes, various other medical therapies and sterilization. The optimal treatment regime for each of these applications may include a different gas, gas flow rate, and other system settings.

Cold Plasma Application Device

Figure 1A:
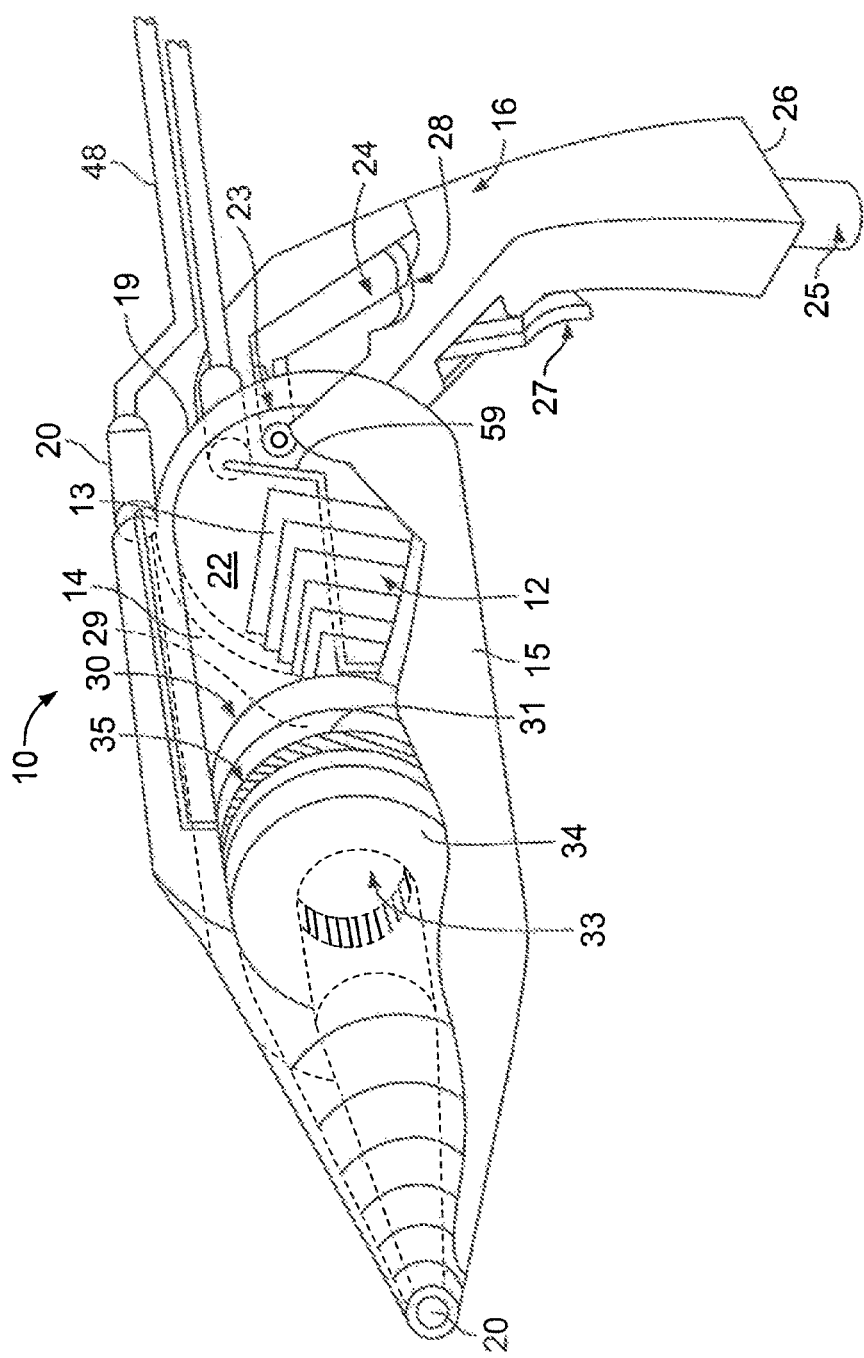
FIGS. 1A and 1B are cutaway views of the hand-held atmospheric harmonic cold plasma device, in accordance with embodiments of the present invention.

To achieve a cold plasma, a cold plasma device typically takes as input a source of appropriate gas and a source of high voltage electrical energy, and outputs a plasma plume. FIG. 1A illustrates such a cold plasma device. Previous work by the inventors in this research area has been described in U.S. Provisional Patent Application No. 60/913,369, U.S. Nonprovisional application Ser. No. 12/038,159 (that has issued as U.S. Pat. No. 7,633,231) and the subsequent continuation applications (collectively "the '369 application family"). The following paragraphs discuss further the subject matter from this application family further, as well as additional developments in this field.

The '369 application family describes a cold plasma device that is supplied with helium gas, connected to a high voltage energy source, and which results in the output of a cold plasma. The temperature of the cold plasma is approximately 65-120 degrees F. (preferably 65-99 degrees F.), and details of the electrode, induction grid and magnet structures are described. The voltage waveforms in the device are illustrated at a typical operating point in '369 application family.

Figure 1B:
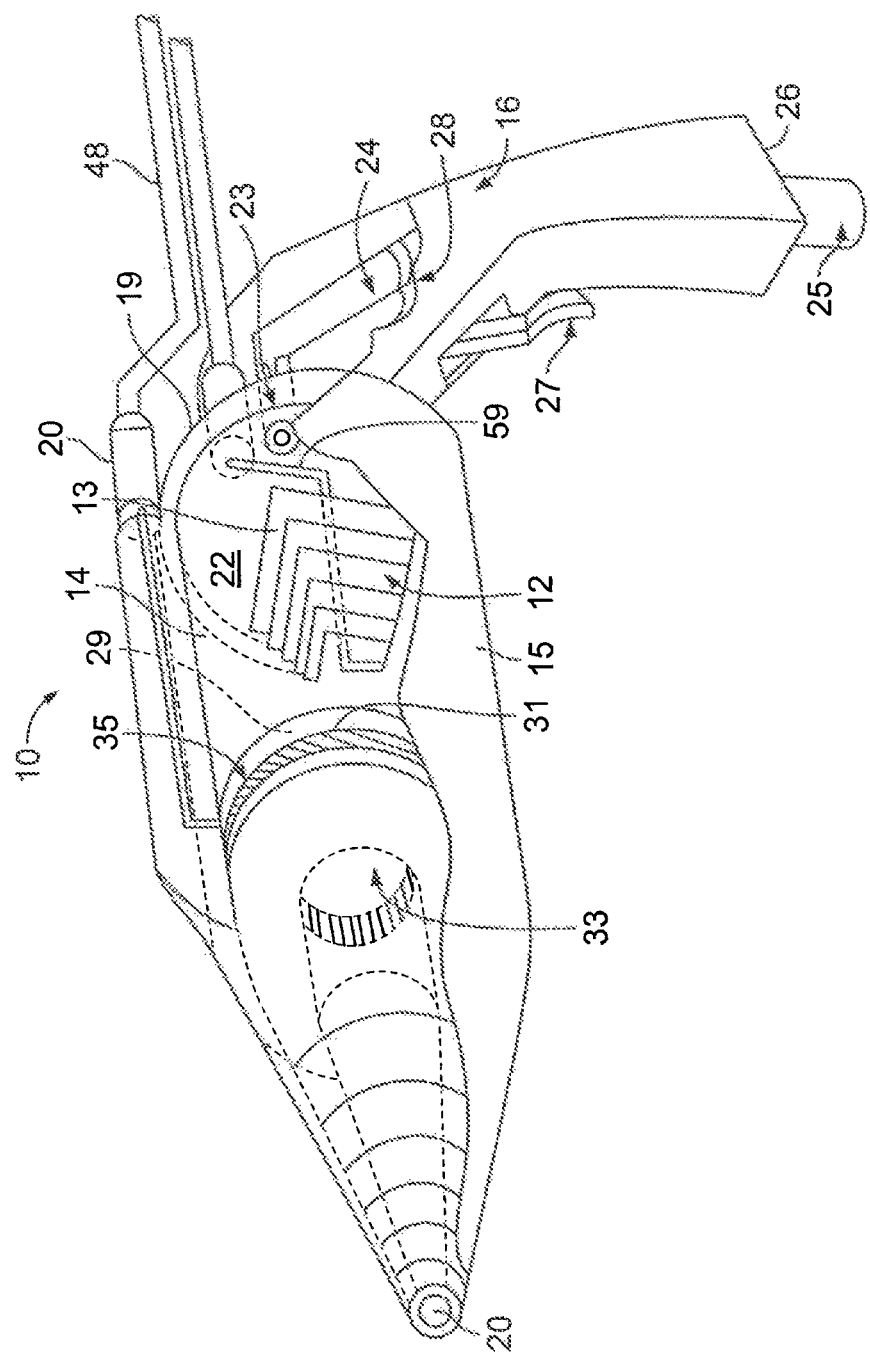
Figure 2A:
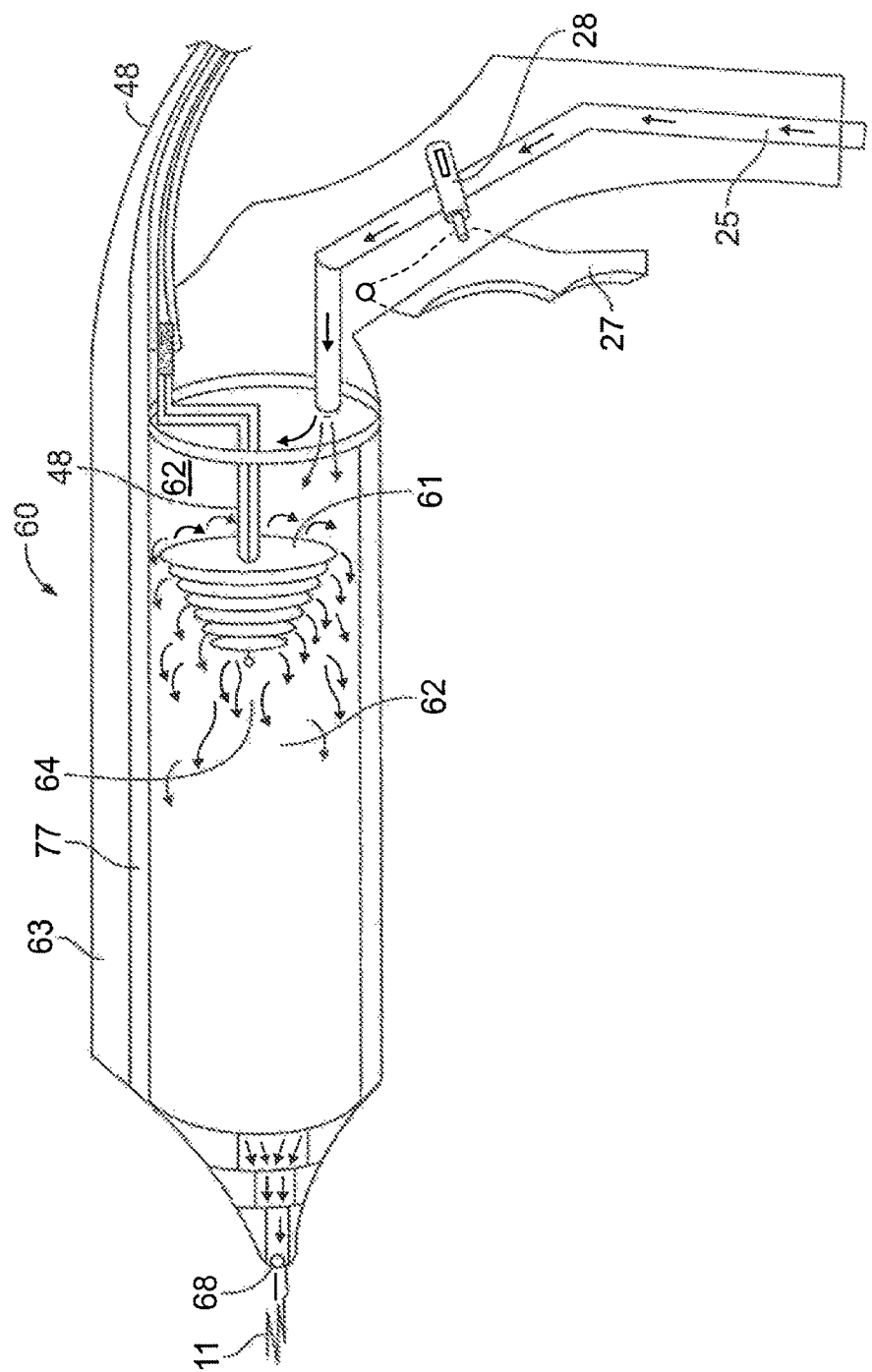
FIGS. 2A and 2B illustrate an embodiment of the cold plasma device without magnets, in accordance with embodiments of the present invention.
Figure 2B:
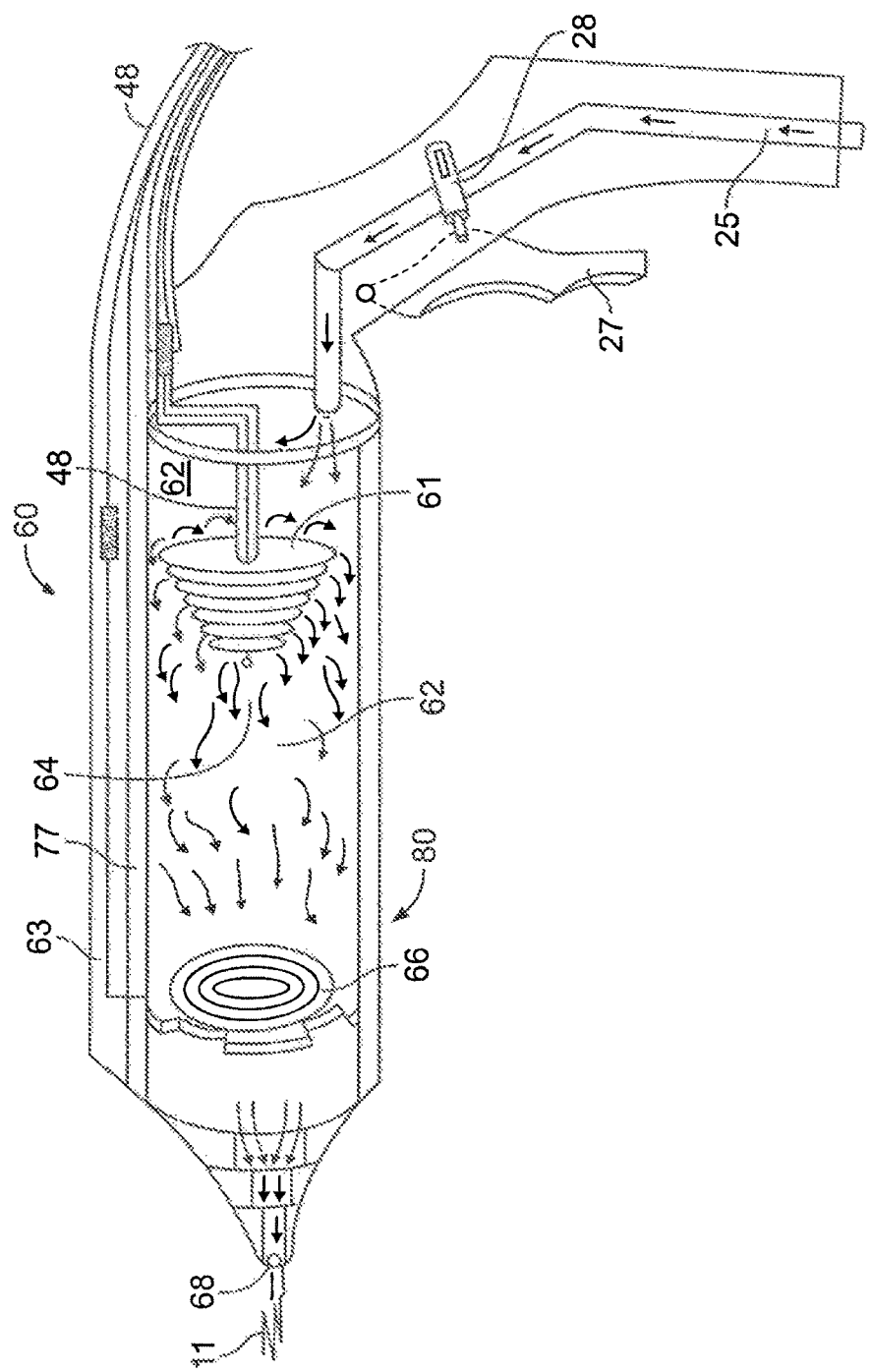

In a further embodiment to that described in the '369 application, plasma is generated using an apparatus without magnets, as illustrated in FIGS. 2A and 2B. In this magnet-free environment, the plasma generated by the action of the electrodes 61 is carried with the fluid flow downstream towards the nozzle 68. FIG. 2A illustrates a magnet-free embodiment in which no induction grid is used. FIG. 2B illustrates a magnet-free embodiment in which induction grid 66 is used. FIG. 1B illustrates the same embodiment as illustrated FIG. 2B, but from a different view. Although these embodiments illustrate the cold plasma is generated from electrode 12, other embodiments do not power the cold plasma device using electrode 12, but instead power the cold plasma device using induction grid 66.

In both a magnet and a magnet-free embodiment, the inductance grid 66 is optional. When inductance grid 66 is present, it provides ionization energy to the gas as the gas passes by. Thus, although the inductance grid 66 is optional, its presence enriches the resulting plasma.

As noted above, the inductance grid 66 is optional. When absent, the plasma will nevertheless transit the cold plasma device and exit at the nozzle 68, although in this case, there will be no additional ionization energy supplied to the gas as it transits the latter stage of the cold plasma device.

As noted with respect to other embodiments, magnetic fields can be used in conjunction with the production of cold plasmas. Where present, magnetic fields act, at least at some level, to constrain the plasma and to guide it through the device. In general, electrically charged particles tend to move along magnetic field lines in spiral trajectories. As noted elsewhere, other embodiments can comprise magnets configured and arranged to produce various magnetic field configurations to suit various design considerations. For example, in one embodiment as described in the previously filed '369 application family, a pair of magnets may be configured to give rise to magnetic fields with opposing directions that act to confine the plasma near the inductance grid.

Cold Plasma Unipolar High Voltage Power Supply

The '369 application family also illustrates an embodiment of the unipolar high voltage power supply architecture and components used therein. The circuit architecture is reproduced here as FIG. 3, and this universal power unit provides electrical power for a variety of embodiments described further below. The architecture of this universal power unit includes a low voltage timer, followed by a preamplifier that feeds a lower step-up voltage transformer. The lower step-up voltage transformer in turn feeds a high frequency resonant inductor-capacitor (LC) circuit that is input to an upper step-up voltage transformer. The output of the upper step-up voltage transformer provides the output from the unipolar high voltage power supply.

Figure 3:
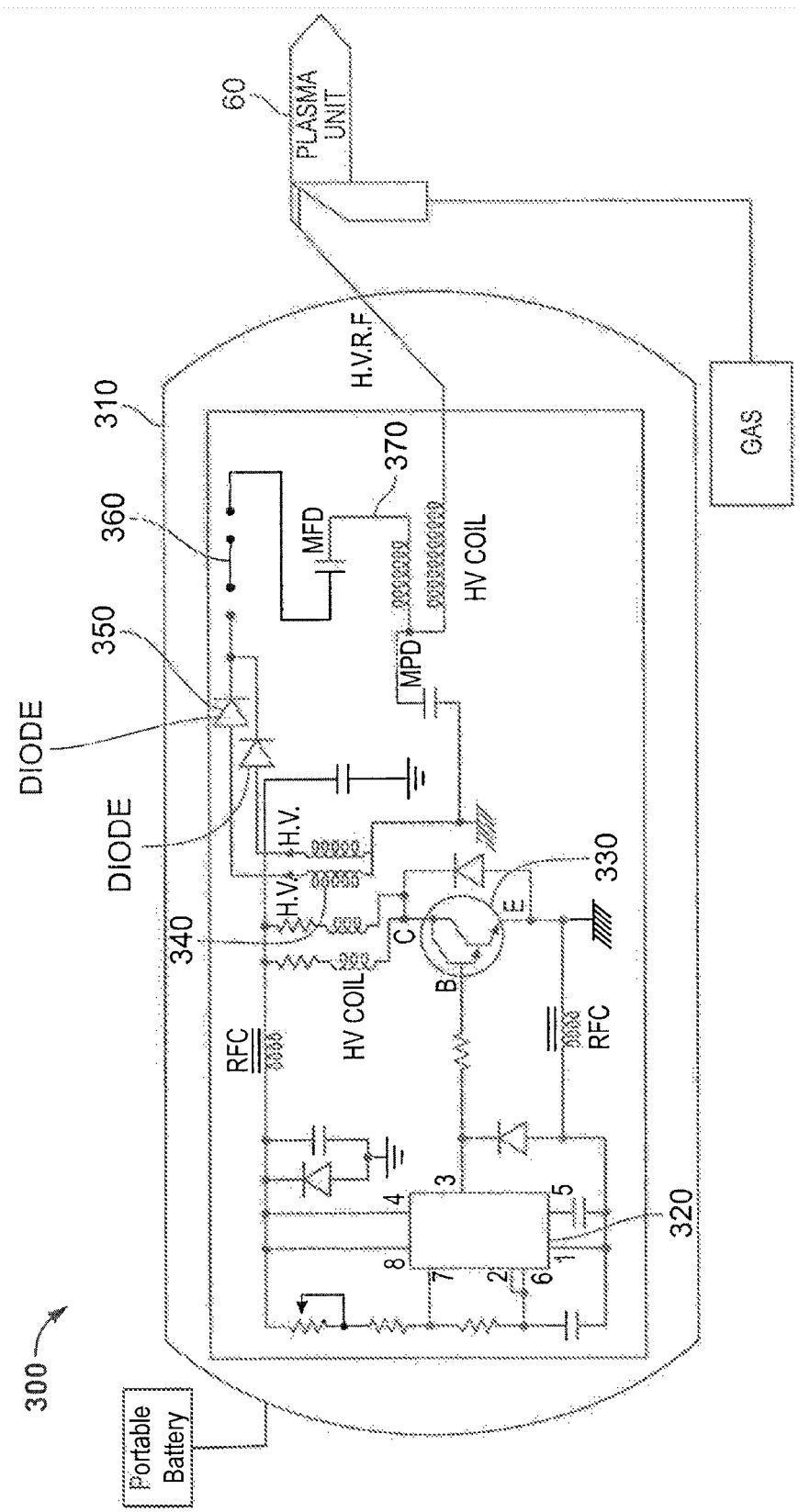
FIG. 3 is an exemplary circuit diagram of the power supply of a cold plasma device, in accordance with embodiments of the present invention.

FIG. 3 also illustrates an exemplary implementation of the unipolar high voltage power supply 310 architecture. In this implementation, a timer integrated circuit such as a 555 timer 320 provides a low voltage pulsed source with a frequency that is tunable over a frequency range centered at approximately 1 kHz. The output of the 555 timer 320 is fed into a preamplifier that is formed from a common emitter bipolar transistor 330 whose load is the primary winding of the lower step-up voltage transformer 340. The collector voltage of the transistor forms the output voltage that is input into the lower step-up voltage transformer. The lower step-up transformer provides a magnification of the voltage to the secondary windings. In turn, the output voltage of the lower step-up voltage transformer is forwarded to a series combination of a high voltage rectifier diode 350, a quenching gap 360 and finally to a series LC resonant circuit 370. As the voltage waveform rises, the rectifier diode conducts, but the quench gap voltage will not have exceeded its breakdown voltage. Accordingly, the quench gap is an open circuit, and therefore the capacitor in the series LC resonant circuit will charge up. Eventually, as the input voltage waveform increases, the voltage across the quench gap exceeds its breakdown voltage, and it arcs over and becomes a short circuit. At this time, the capacitor stops charging and begins to discharge. The energy stored in the capacitor is discharged via the tank circuit formed by the series LC connection.

Continuing to refer to FIG. 3, the inductor also forms the primary winding of the upper step-up voltage transformer 340. Thus, the voltage across the inductor of the LC circuit will resonate at the resonant frequency of the LC circuit 370, and in turn will be further stepped-up at the secondary winding of the upper step-up voltage transformer. The resonant frequency of the LC circuit 370 can be set to in the high kHz-low MHz range. The voltage at the secondary winding of the upper step-up transformer is connected to the output of the power supply unit for delivery to the cold plasma device. The typical output voltage is in the 10-150 kV voltage range. Thus, voltage pulses having a frequency in the high kHz-low MHz range can be generated with an adjustable repetition frequency in the 1 kHz range. The output waveform is shaped similar to the acoustic waveform generated by an impulse such as a bell is struck with a hammer. Here, the impulse is provided when the spark gap (or SCR) fires and produces the voltage pulse which causes the resonant circuits in the primary and secondary sides of the transformer to resonate at their specific resonant frequencies. The resonant frequencies of the primary and the secondary windings are different. As a result, the two signals mix and produce the unique 'harmonic' waveform seen in the transformer output. The net result of the unipolar high voltage power supply is the production of a high voltage waveform with a novel "electrical signature," which when combined with a noble gas or other suitable gas, produces a unique harmonic cold plasma that provides advantageous results in wound healing, bacterial removal and other applications.

The quenching gap 360 is a component of the unipolar high voltage power supply 310. It modulates the push/pull of electrical energy between the capacitance banks, with the resulting generation of electrical energy that is rich in harmonic content. The quenching gap can be accomplished in a number of different ways, including a sealed spark gap and an unsealed spark gap. The sealed spark gap is not adjustable, while unsealed spark gaps can be adjustable. A sealed spark gap can be realized using, for example, a DECI-ARC 3000 V gas tube from Reynolds Industries, Inc. Adjustable spark gaps provide the opportunity to adjust the output of the unipolar high voltage power supply and the intensity of the cold plasma device to which it is connected. In a further embodiment of the present invention that incorporates a sealed (and therefore non-adjustable) spark gap, thereby ensuring a stable plasma intensity.

In an exemplary embodiment of the unipolar high voltage power supply, a 555 timer 320 is used to provide a pulse repetition frequency of approximately 150-600 Hz. As discussed above, the unipolar high voltage power supply produces a series of spark gap discharge pulses based on the pulse repetition frequency. The spark gap discharge pulses have a very narrow pulse width due to the extremely rapid discharge of capacitive stored energy across the spark gap. Initial assessments of the pulse width of the spark gap discharge pulses indicate that the pulse width is approximately 1 nsec. The spark gap discharge pulse train can be described or modeled as a filtered pulse train. In particular, a simple resistor-inductor-capacitor (RLC) filter can be used to model the capacitor, high voltage coil and series resistance of the unipolar high voltage power supply. In one embodiment of the invention, the spark gap discharge pulse train can be modeled as a simple modeled RLC frequency response centered in the range of around 100 MHz. Based on the pulse repetition frequency of 192 Hz, straightforward signal analysis indicates that there would be approximately 2,000,000 individual harmonic components between DC and 400 MHz.

In another embodiment of the unipolar high voltage power supply described above, a 556 timer or any timer circuit can be used in place of the 555 timer 320. In comparison with the 555 timer, the 556 timer provides a wider frequency tuning range that results in greater stability and improved cadence of the unipolar high voltage power supply when used in conjunction with the cold plasma device.

In a further embodiment of the high voltage power supply, a smart electronics feature can be added to the high voltage power supply. With this feature added, the high voltage power supply can recognize the type of cold plasma hand piece that is connected to the high voltage power supply, and adjust the power supply output accordingly. For example, with a different hand piece, the output voltage, output resonant frequency or timer frequency can be adjusted to support the particular hand piece being used. In a further embodiment, the smart electronics can recognize not only the particular hand piece being connected to the power supply, but also one or more of the particular nozzles (tips) being connected at the gas outlet of the hand piece and the composition of gas and the duration of treatment based on the connection at the gas inlet. Based on being able to sense the nozzle-hand-piece combination, predetermined box settings can be automatically made by the power supply in response to these sensed configurations. The sensing process can be accomplished by any of the numerous methods by which such configuration data can be obtained. For example, the coding of the hand-piece and/or nozzle can be performed via an ID chip (e.g., a RFID chip), which can be read remotely by the appropriate RFID interrogator installed in the high voltage power supply. Other alternative means of information storage include electrically erasable programmable read only memory (EEPROM). Other alternatives for the sensing include the use of a simple mechanical-electrical connection such as pin connectors or the use of printed metal stripes (similar to a barcode) on the surface of the nozzle or gas cartridge (to be discussed further below) that physically makes the desired connection. The configuration data can include the hand-piece-nozzle configuration, or could also contain information such as safety and other information (such as maximums and minimums) that are set by various regulatory and other authorities. For example, the data memory can indicate the maximum time to which a particular treatment area can be exposed. Where more complex relationships apply to various relevant operating parameters, such information can also be stored in the data memory. In addition to remote sensing of the data memory, wired and/or wireless connectivity can be provided to make the relevant information available to the high voltage power supply. In response to the received data, the high voltage power supply responds automatically by making the appropriate settings, such as low frequency, resonant high frequency, output voltage, gas flow rates and time of operation.

Gas Cartridges

Evaluations of the use of cold plasma treatments has revealed that such treatments use a particular treatment time, using a particular amount of gas having a particular composition of gas, with a particular electrical setting in the handpiece. Conventional wisdom had suggested that length of cold plasma treatment could be arbitrary, and that a medical professional might have had considerable discretion in selecting the amount of time for each cold plasma treatment. However, studies have revealed that, contrary to the conventional wisdom, a particular treatment time using a particular amount of gas is effective for many applications. Such a revelation on the relevance of a particular amount of gas provides the opportunity for the use of gas cartridges of various sizes that are relevant to particular treatments.

As an example, for a sterilization and accelerated healing of a laceration, one cold plasma treatment regimen involves the use of 30 seconds of helium gas. Other medical treatment regimens for other medical applications use other gas compositions and other gas volumes. Use of a gas cartridge having the required volume and gas composition appropriate for the treatment regimen reduces errors in the use, safety and efficacy of cold plasma treatments.

FIG. 4A illustrates a gas cartridge 400, in accordance with an embodiment of the present invention. In this embodiment, gas cartridge 400 is cylindrical in shape, and has a bulbous shape similar to a bottle. Gas cartridge 400 has a bottle neck 410 at its distal end 420. Gas cartridge 400 can be manufactured from any suitable material that can contain the gas, such as a metal, heavy duty plastic, and the like. Gas cartridge 400 can use a threaded connector for connection, or any other suitable connection arrangement, such as quarter-turn connections, half-turn connections and the like. Connector 430 is located at distal end 420, and is configured to be connected to cold plasma hand-piece. In other embodiments of the present invention, gas cartridge 400 is not limited to a bulbous (bottle-like) shape, as other shapes are within the scope of the present invention. Internal to gas cartridge 400 is a gas storage compartment 440 containing the appropriate quantity (typically under pressure) of the appropriate gas composition for delivery to the cold plasma hand-piece. Prior to being connected, connector 430 maintains a seal that prevents the gas stored in gas storage compartment 440 to leave gas cartridge 400. When connected, connector 430 allows gas stored in gas storage compartment 440 to leave gas cartridge 400. To prevent leakage of gas in the connection, a gasket can be provided in each gas cartridge 400. Alternatively, a gasket can be provided in the mating connector in the cold plasma hand-piece (or in the power supply in other embodiments), with the benefit being a single gasket rather than a gasket required for each gas cartridge 400. In an embodiment, connector 430 has an endcap (or faceseal) 450 placed across the outlet of gas cartridge 400. Endcap 450 provides the seal across the face of the outlet of gas cartridge 400 to prevent escape of the gas. Endcap 450 can be manufactured from any suitable material (e.g., metallic material) to maintain the seal in gas cartridge 400.

With further reference to FIG. 4B, mating connector 470 in a cold plasma delivery system includes a pin 460 that is typically in the center of mating connector 470. Pin 460 punctures endcap 450 upon the connection of connector 430 and its mating connector. Mating connector 470 can be located either in the cold plasma hand-piece or in the high voltage power supply of the cold plasma delivery system. When the stored gas in gas cartridge 400 is under pressure, the cold plasma hand-piece needs to incorporate a pressure reducing valve and flow regulator. For embodiments where gas cartridge 400 connects to the high voltage power supply, the pressure reducing valve and flow regulator can be incorporated into either the high voltage power supply or cold plasma hand-piece. In most cases, the pressure reducing valve and flow regulator would be incorporated into a cold plasma hand-piece. In certain embodiments of the present invention, connector 430 (and its mating connector 470) can be designed to incorporate safety features such that only connectors designed for mating with the cold plasma gun or the power unit of the cold plasma delivery system can make the desired connection.

In an exemplary embodiment, gas cartridge 400 can contain 2.4 grams of helium gas. In gas cartridge 400, connector 430 is a threaded connector that can connect into a compatible receiving port in the cold plasma delivery system, either the cold plasma hand-piece or the high voltage power unit.

Figure 5A:
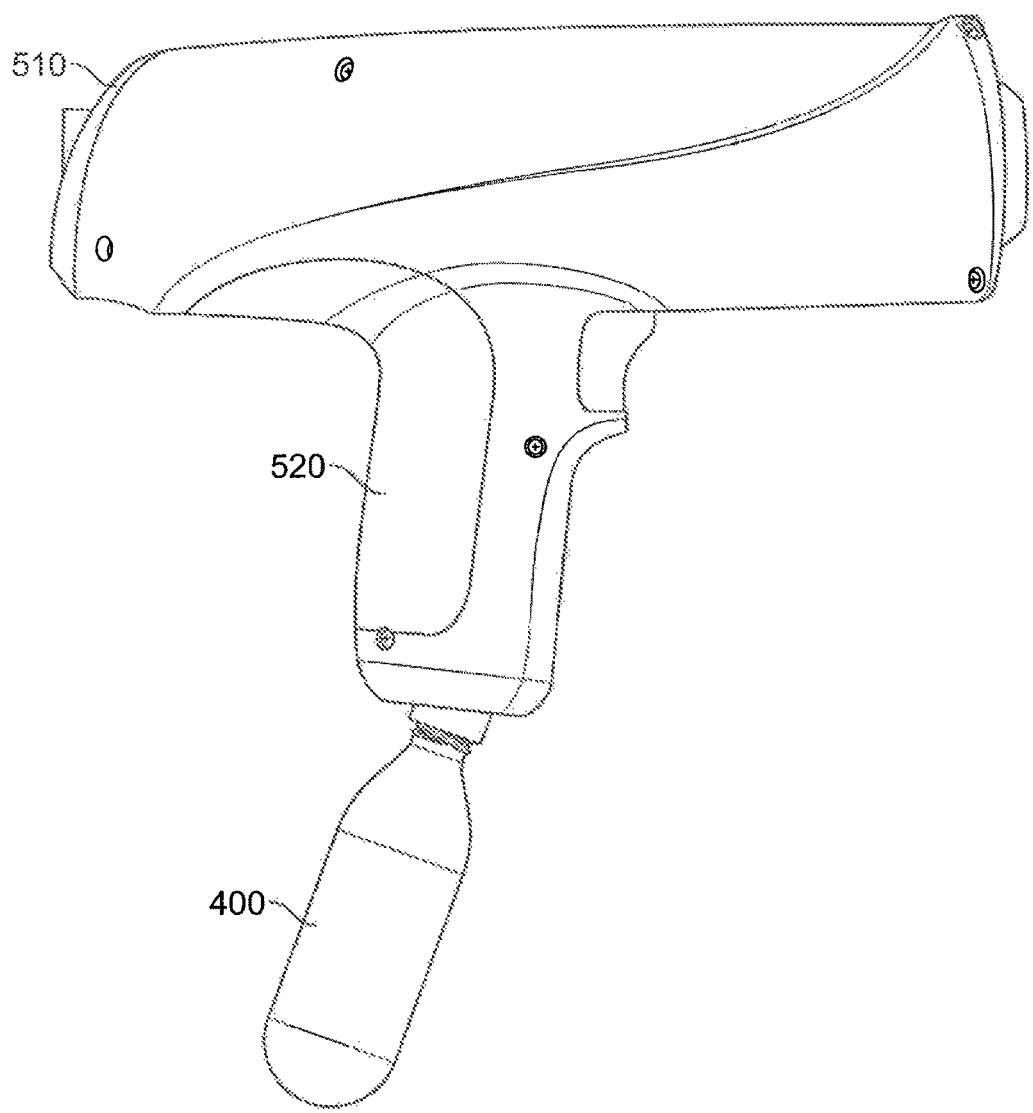
FIGS. 5A and 5B illustrate different connections of a gas cartridge within a cold plasma delivery system, in accordance with an embodiment of the present invention.
Figure 5B:
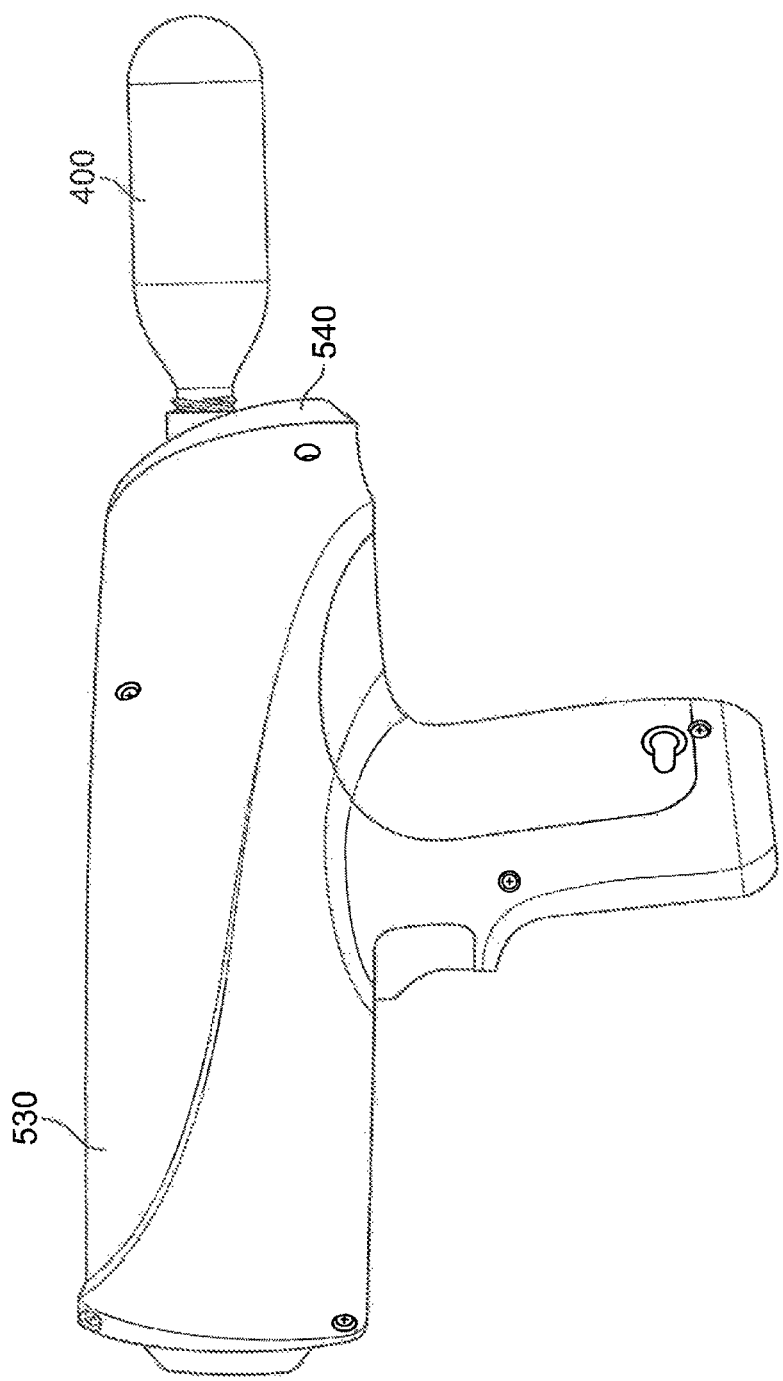

Suitable mating connector locations in the cold plasma hand-piece can be in any number of suitable places, such that the gas can enter the chamber of the hand-piece at a suitable up-stream location consistent with the cold plasma generation process. FIGS. 5A and 5B illustrate various embodiments with different locations of the connection between gas cartridge 400 and the cold plasma hand-piece. In one exemplary embodiment (illustrated in FIG. 5A), the connection between gas cartridge 400 and cold plasma device 510 is located at the base of the hand-grip 520 of the cold plasma hand-piece 510. In an alternative exemplary embodiment (illustrated in FIG. 5B), the connection between gas cartridge 400 and cold plasma hand-piece 530 is located in the rearward end 540 of the cold plasma hand-piece 530. In both embodiments, the gas is routed internally within the cold plasma hand-piece to its gas compartment. In a still further embodiment (not illustrated), gas cartridge 400 can be connected to the high voltage power supply, with the high voltage power supply in tarn communicating the gas to the cold plasma hand-piece.

For embodiments where gas cartridge 400 is connected to cold plasma hand-piece 610, an optional protective shroud 620 can encase the gas cartridge 400 when it is connected to the cold plasma hand-piece 610. FIG. 6 illustrates an optional protective shroud 620 can be made of any suitable material to prevent damage to a user should gas cartridge 400 explode or disintegrate.

In addition, the gas cartridge can be electronically or otherwise coded so that its connection to the cold plasma hand-piece triggers the high voltage power supply to apply the correct voltage, frequency and other related parameters. The coding can be via an ID chip (e.g., a RFID chip) or any other electronic means for storing a particular ID number that can be read by a nearby device such as the power supply. In addition, for ease of use, cartridge can be color coded, as well as labeled, so that medical professionals can recognize the appropriate cartridge for the desired treatment. This embodiment allows for ease of use, convenience, and portability of the cold plasma hand-piece and cold plasma delivery system. In particular, it provides only enough gas for a given procedure, i.e., is procedure specific. Accordingly, it improves safety of procedure, and the proper use of helium and various other gases (e.g., $O_2$, $N_2$, water vapor, argon and the like) and mixtures of these gases.

Disposable gas cartridges, with an ID chip, ensure the gas or gas mixture is compatible with the plasma medical device and settings are appropriate to further ensure safe operation and therefore the effectiveness of treatment, along with the purity/sterility of the gas. This will also function to make sure the pressure is not too high as to damage the machine, and work to eliminate variability between regions and gas suppliers. Lastly, the ID chipped disposable gas cartridges will ensure strict control of the treatment duration for safety and efficacy.

When treating open wounds with an instrument such as cold plasma, it is important to ensure that no new pathogens are introduced to the wound and that pathogens are not spread from patient to patient. Therefore, it is desirable to have a, prepackaged, and easily exchangeable gas cartridge that can be disposed of and replaced between each use. Further, different wound types may warrant different gas compositions or volumes to supply and/or modify the plasma plume for a patient-specific approach to plasma wound therapy. The following additional embodiments seek to meet these needs with disposable gas cartridges capable of generating a unique and varied plasma plume of compositional make-up providing suitable reactive species of gas and/or discrete treatment duration.

The cartridge may be provided in sterile or non-sterile packaging depending upon its intended use. For example, a cartridge mounted in the hand applicator and intended for use in the sterile field of an operating room might require sterilization and packaging, while a cartridge disposed within the power unit and intended for treatment in an outpatient setting may not require sterile handling and packaging. In either case, the gas should be of medical grade, high purity, and sterile.

In another embodiment (not illustrated), it may be more desirable to have the gas cartridge attached to the high voltage power unit, rather than directly to the applicator. Advantages of this embodiment are: (a) reduced safety risk if the cold plasma device is dropped with a full gas cartridge attached; (b) greater ease to incorporate an RFID reader or other sensor into the power supply unit rather than into the hand device; (c) the absence of the attached gas cartridge results in an improved ergonomic balance and feel of the hand device; and (d) potential reduction in manufacture cost of the hand held device as the gas regulation is performed remotely. When a high pressure cartridge is connected to the hand piece directly (FIGS. 5A and 5B), a pressure reducing valve and flow regulator must be incorporated into the plasma hand unit. In '631 patent, the regulator/flow control is external and on the tank. If the cartridge resides in the power unit, regulator and pressure reduction can still be accomplished remotely from the hand applicator, per the '631 patent.

Gas Cartridge Methods

FIG. 7 provides a flowchart of an exemplary method 700 to use a gas cartridge with a cold plasma device, according to an embodiment of the present invention.

The process begins at step 710. In step 710, a gas cartridge is provided, the gas cartridge containing a suitable amount of gas, the gas cartridge having a connector that includes a seal to prevent the gas from escaping. In an embodiment, a gas cartridge 400 is configured to couple to cold plasma device 510.

In step 720, a cold plasma hand piece is provided, the cold plasma hand piece having a mating connector to the connector in the gas cartridge, where the mating connector that pierces the seal when the mating connector is connected to the gas cartridge connector. In an exemplary embodiment, a seal 450 in gas cartridge 400 is pierced when gas cartridge 400 is connected to cold plasma device 510.

In step 730, the gas cartridge is connected to the cold plasma hand piece using the connector and the mating connector. In an exemplary embodiment, gas cartridge 400 is connected to cold plasma hand-pieces 510, 530 using connector 430 and a mating connector 470 in cold plasma hand-pieces 510, 530.

At step 740, method 700 ends.

FIG. 8 provides a flowchart of a further exemplary method 800 to use a gas cartridge with a cold plasma device, according to an embodiment of the present invention.

The process begins at step 810. In step 810, a gas cartridge is provided, the gas cartridge containing a suitable amount of gas, the gas cartridge having a connector that includes a seal to prevent the gas from escaping. In an embodiment, a gas cartridge 400 is configured to couple to a high voltage power supply.

In step 820, a cold plasma device and a pulsed high voltage power supply are provided, the high voltage power supply having a mating connector to the connector in the gas cartridge, where the mating connector that pierces the seal when the mating connector is connected to the gas cartridge connector. In an exemplary embodiment, a seal 450 in gas cartridge 400 is pierced when gas cartridge 400 is connected to the high voltage power supply.

In step 830, the gas cartridge is connected to pulsed high voltage power supply using the connector and the mating connector. In an exemplary embodiment, gas passes from gas cartridge 400 to the high voltage power supply and forwarded to cold plasma device 510.

In step 840, the pulsed high voltage power supply determines the type of gas cartridge connected. In an exemplary embodiment, pulsed high voltage power supply determines the type of gas cartridge 510 connected. Determination of the type of gas cartridge can be achieved by a keyed physical feature on the cartridge, an RFID tag on the cartridge, an electronic microchip on the cartridge, a bar code on the cartridge, a magnetic tag on the cartridge, or an optically readable tag on the cartridge.

In step 850, the pulsed high voltage power supply adjusts one or more of its operating parameters based on the type of connected gas cartridge.

In step 860, the pulsed high voltage power supply applies voltage to cold plasma hand piece.

In step 870, method 800 ends.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A cold plasma device, comprising:
    a housing having a high voltage electrical inlet port and a gas compartment, the gas compartment having a gas inlet port and a gas outlet port, wherein the gas inlet and gas outlet ports are adapted to sense configurations associated with the gas inlet and gas outlet ports respectively;
    an electrode disposed within the gas compartment, wherein the electrode is coupled to the high voltage electrical inlet port; and
    a high voltage power supply coupled to the high voltage electrical inlet port, wherein the high voltage power supply is configured to sense the configuration of the gas outlet port and wherein the high voltage power supply is configured to adjust its operating parameters in response to the sensed gas outlet port configuration.

2. The cold plasma device of claim 1, wherein the gas inlet port is adapted to sense a gas composition and duration of treatment, and wherein the gas outlet port is adapted to sense a shape of a plasma delivery port.

3. The cold plasma device of claim 1, further comprising:
    a portable battery coupled to the high voltage power supply, the high voltage power supply being configured to be powered by energy from the portable battery.

4. The cold plasma device of claim 1, wherein the operating parameters adjusted include one or more of voltage, frequency, gas flow rate, gas pressure and treatment duration.

5. The cold plasma device of claim 1, wherein the configuration associated with the gas inlet port includes a gas cartridge comprising:
    a storage compartment for use with the cold plasma device, wherein the storage compartment is configured to store a quantity of gas suitable for use in the cold plasma device in a single treatment session; and
    an outlet with a connector having a seal across the outlet, the connector configured for use with the cold plasma device or the high voltage power supply associated with the cold plasma device, and the seal configured to be broken upon connection with the cold plasma device or the associated high voltage power supply.

6. The cold plasma device of claim 5, wherein the seal is a metallic endcap.

7. The cold plasma device of claim 5, wherein the connector includes a screw thread.

8. The cold plasma device of claim 5. wherein the quantity of gas includes a quantity of helium.

9. The cold plasma device of claim 5, wherein the gas cartridge has a bottle shape.

10. The cold plasma device of claim 5, wherein the seal is configured to be broken by a pin associated with the cold plasma device.

11. The cold plasma device of claim 1, wherein the configuration associated with the gas inlet port includes
    a gas cartridge comprising:
        a storage compartment for use with the cold plasma device, wherein the storage compartment is configured to store a quantity of gas sufficient for a specific medical process; and
    an outlet with a connector having a seal across the outlet, the connector configured for use with the cold plasma device or the high voltage power supply associated with the cold plasma device, and the seal configured to be broken upon connection with the cold plasma device or the associated high voltage power supply.

12. The cold plasma device of claim 11, wherein the seal is a metallic endcap.

13. The cold plasma device of claim 11, wherein the connector includes a screw thread.

14. The cold plasma device of claim 11, wherein the quantity of gas includes a quantity of helium.

15. The cold plasma device of claim 11, wherein the gas cartridge has a bottle shape.

16. The cold plasma device of claim 11, wherein the seal is configured to be broken by a pin associated with the cold plasma device.

17. The cold plasma device of claim 11, wherein the cold plasma device is configured to receive the gas cartridge by a mating connector located within a hand-grip of the cold plasma device.

18. The cold plasma device of claim 11, wherein the cold plasma device is configured to receive the gas cartridge by a mating connector located within a rearward end of the cold plasma device.

19. The cold plasma device of claim 18, further comprising:
a shroud attached to the housing, the shroud enclosing the gas cartridge to reduce safety risk associated with a dropping of the cold plasma device.

20. The cold plasma device of claim 11,
wherein the high voltage power supply is configured to receive the gas cartridge by a mating connector, and the high voltage power supply is configured to receive the gas cartridge by mating connector, and the high voltage power supply is further configured to transfer gas emanting from the gas cartridge to the gas compartment of the cold plasma device.

21. A method comprising:
providing a gas cartridge, the gas cartridge containing an amount of gas suitable for use in a single treatment session using cold plasma, the gas cartridge having a connector;
providing a pulsed high voltage power supply, the pulsed high voltage power supply having a mating connector to the connector in the gas cartridge;
connecting the gas cartridge to the pulsed high voltage power supply using the connector and the mating connector;
determining, by the pulsed high voltage power supply, a type of gas cartridge, wherein the determining includes using a sensor associated with the gas cartridge;
adjusting one or more operating parameters of the pulsed high voltage power supply based on the type of gas cartridge; and
providing a cold plasma hand piece, the cold plasma hand piece configured to receive the gas and energy from the pulsed high voltage power supply.

22. The method of claim 21, wherein the determining the type of gas cartridge includes using at least one of a keyed physical feature on the cartridge, an RFID tag on the cartridge, an electronic microchip on the cartridge, an EPROM on the cartridge, a bar code on the cartridge, a magnetic tag on the cartridge, or an optically readable tag on the cartridge.

23. The method of claim 21, wherein the adjusting the operating parameters of the pulsed high voltage power supply includes adjusting at least one of pulse frequency, resonance frequency, output voltage or treatment duration.

* * * * *

UNITED STATES PATENT AND TRADEMARK OFFICE
CERTIFICATE OF CORRECTION

PATENT NO. : 9,257,264 B2  Page 1 of 1
APPLICATION NO. : 13/620132
DATED : February 9, 2016
INVENTOR(S) : Hummel et al.

It is certified that error appears in the above-identified patent and that said Letters Patent is hereby corrected as shown below:

In the Claims

Column 11, lines 32-35, replace "by a mating connector, and the high voltage power supply is configured to receive the gas cartridge by mating connector, and" with --by a mating connector, and--.

Column 12, line 26, replace "EPROM" with --EEPROM--.

Signed and Sealed this
Tenth Day of May, 2016

Michelle K. Lee
*Director of the United States Patent and Trademark Office*